(12) United States Patent
McDaniel

(10) Patent No.: US 9,987,480 B2
(45) Date of Patent: *Jun. 5, 2018

(54) PRESSURE CONTROLLED MAGNETIC VALVE FOR A CATHETER

(71) Applicant: Michael R. McDaniel, Kissimmee, FL (US)

(72) Inventor: Michael R. McDaniel, Kissimmee, FL (US)

(73) Assignee: Infinity Medical Engineering, LLC

( * ) Notice: Subject to any disclaimer, the term of this patent is extended or adjusted under 35 U.S.C. 154(b) by 78 days.

This patent is subject to a terminal disclaimer.

(21) Appl. No.: 15/137,101

(22) Filed: Apr. 25, 2016

(65) Prior Publication Data

US 2016/0235963 A1    Aug. 18, 2016

Related U.S. Application Data

(63) Continuation of application No. 14/156,690, filed on Jan. 16, 2014, now Pat. No. 9,320,882.

(Continued)

(51) Int. Cl.
*A61M 39/22* (2006.01)
*A61F 5/44* (2006.01)
(Continued)

(52) U.S. Cl.
CPC .......... *A61M 39/22* (2013.01); *A61F 5/4404* (2013.01); *A61F 5/4405* (2013.01);
(Continued)

(58) Field of Classification Search
CPC ..... A61F 5/4404; A61F 5/4405; A61M 39/22; A61M 39/227; F16K 27/0227;
(Continued)

(56) References Cited

U.S. PATENT DOCUMENTS 2,646,071 A * 7/1953 Wagner ................. F16K 15/023
137/528
2,949,931 A * 8/1960 Ruppright ............... F16K 15/02
137/515.7

(Continued)

FOREIGN PATENT DOCUMENTS

EP      0 700 688 A1    3/1996
GB      1351196         4/1974
(Continued)

*Primary Examiner* — Adam Marcetich
(74) *Attorney, Agent, or Firm* — Robert M. Schwartz; Alfred K. Dassler

(57) ABSTRACT

A urine control device to be placed intermediate a catheter and a collection bag is provided. The urine control device includes first and second bell shaped housings with a magnetic valve disposed between the first and the second housings. When the pressure from the urine which flows through the present catheter enters the first chamber and exceeds the magnetic attraction in the valve, the valve pivotally opens, permitting the urine to flow through the open valve and into the second chamber. Due to the shape of the chambers, secondary forces create a low pressure zone in the second chamber which helps empty the bladder fully. Once the flow ceases, the magnetic valve pivotally shuts, allowing the urine pressure to build once again. Various sample ports and air entry ports may be provided on the device.

9 Claims, 14 Drawing Sheets

Related U.S. Application Data

(60) Provisional application No. 61/927,916, filed on Jan. 15, 2014, provisional application No. 61/927,078, filed on Jan. 14, 2014, provisional application No. 61/753,020, filed on Jan. 16, 2013.

(51) Int. Cl.
*F16K 27/02* (2006.01)
*F16K 31/08* (2006.01)

(52) U.S. Cl.
CPC ....... *A61M 39/227* (2013.01); *F16K 27/0227* (2013.01); *F16K 31/084* (2013.01); *F16K 31/088* (2013.01); *F16K 31/08* (2013.01); *F16K 31/086* (2013.01)

(58) Field of Classification Search
CPC ...... F16K 31/08; F16K 31/084; F16K 31/086; F16K 31/088
See application file for complete search history.

(56) References Cited

U.S. PATENT DOCUMENTS

| | | | | |
|---|---|---|---|---|
| 3,370,305 A | * | 2/1968 | Goott | A61F 2/2403 137/527 |
| 3,409,038 A | * | 11/1968 | Blackford | F16K 15/08 137/516.15 |
| 3,731,670 A | * | 5/1973 | Loe | A61F 6/24 128/831 |
| 3,774,611 A | * | 11/1973 | Tussey | A61M 1/0011 417/472 |
| 3,900,029 A | * | 8/1975 | Melnick | A61M 1/0011 251/65 |
| 3,905,391 A | | 9/1975 | Oakes | |
| 4,275,759 A | * | 6/1981 | Huang | F16K 15/021 137/528 |
| 4,865,588 A | * | 9/1989 | Flinchbaugh | A61F 5/4405 128/DIG. 25 |
| 4,874,012 A | * | 10/1989 | Velie | F16K 17/34 137/521 |
| 5,366,506 A | * | 11/1994 | Davis | A61F 2/0018 600/29 |
| 7,255,323 B1 | * | 8/2007 | Kadhim | F16K 17/26 137/529 |
| 2002/0189687 A1 | * | 12/2002 | Linthorst | F16K 15/026 137/522 |
| 2008/0060701 A1 | * | 3/2008 | Kim | F16K 17/363 137/38 |

FOREIGN PATENT DOCUMENTS

| | | |
|---|---|---|
| WO | WO 00/02499 | 1/2000 |
| WO | WO 02/087409 | 11/2002 |
| WO | WO 2012/154781 | 11/2012 |

\* cited by examiner

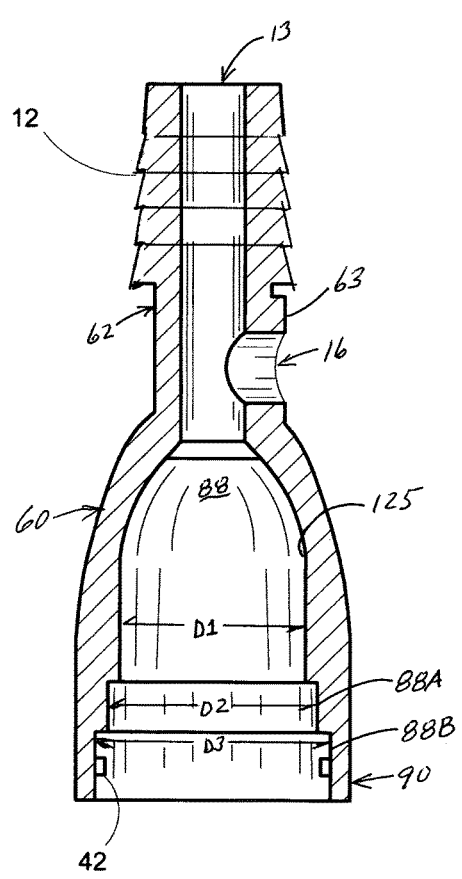
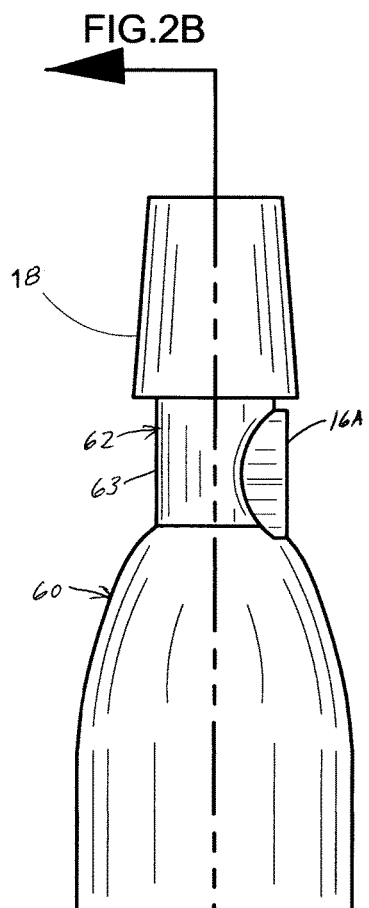
FIG.2A
FIG.2B (SECTION THRU FIG.10A)

(SECTION THRU FIG.10A)

PRESSURE CONTROLLED MAGNETIC VALVE FOR A CATHETER

INDEX TO RELATED APPLICATIONS

This application is a continuation application of U.S. patent application Ser. No. 14/156,690, filed Jan. 16, 2014, entitled Pressure Controlled Magnetic Valve For A Catheter, which claims the benefit of U.S. Provisional Patent Application Ser. No. 61/753,020 filed on Jan. 16, 2013, U.S. Provisional Patent Application Ser. No. 61/927,078 filed on Jan. 14, 2014, and of U.S. Provisional Patent Application Ser. No. 61/927,916 filed on Jan. 15, 2014, the disclosures of which are incorporated herein by reference in their entirety.

BACKGROUND OF THE INVENTION

The use of a catheter to allow a patient to micturate while undergoing medical treatment or for other reasons is well known. One common catheter of this type is known as a Foley catheter. A Foley catheter is a flexible tube that is passed through the urethra and into the bladder. The tube has two separate channels, or lumens, running down its length. One lumen is open at both ends, and allows urine to drain out into a collection bag. The other lumen has a valve on the outside end and connects to a balloon at the tip; the balloon is inflated with sterile water when it lies inside the bladder, in order to stop it from slipping out. Foley catheters are commonly made from silicone rubber or natural rubber.

The name comes from the designer, Dr. F. Foley a surgeon working in Boston Mass. in the 1930s. His original design was adopted by C. R. Bard and Company of Murray Hill, N.J., who manufactured the first prototypes and named them in honor of the surgeon.

The relative size of a Foley catheter is described using French Units (F). The most common sizes are 10 French to 28 French. A catheter of 1 French has a diameter of 0.33 mm.

Foley catheters come in several sub-types: "Coudé" (French for elbowed) catheters have a 45° bend at the tip to allow easier passage through an enlarged prostrate. "Council tip" catheters have a small hole at the tip which allows them to be passed over a wire. "Three way" or "triple lumen" catheters have a third channel, which is used to infuse sterile saline or another irrigating solution. These are used primarily after surgery on the bladder or prostrate, to wash away blood and blood clots.

A major problem with Foley catheters is that they have a tendency to contribute to urinary tract infections (UTI). This occurs because bacteria can travel up the catheters to the bladder where the urine can become infected. To combat this, the industry is moving to antiseptic coated catheters. This has been helpful, but it has not completely solved this major problem. An additional problem is that Foley catheters tend to become coated over time with a bio-film that can obstruct the drainage. This increases the amount of stagnant urine left in the bladder, which further contributes to the problem of urinary tract infections. When a Foley catheter becomes clogged, it must be flushed or replaced.

In addition, long term use of such catheters may result in the shrinkage of the bladder, and a loss of muscle tone in the muscles used to control urine flow. In this case when the catheter is removed, incontinence may result. The present invention overcomes these problems and can be employed with any catheter and is not limited to a Foley catheter.

These and other problems with catheter usage will be solved by use of the invention described below.

BRIEF SUMMARY OF THE INVENTION

The invention comprises a urine flow control device which is placed in a urine flow lumen intermediate the bladder and the urine collection bag. The urine flow control device is external to the human body. The urine flow control device comprises an input port which is connected to the urine flow lumen on the top and then into an input housing. The input housing is adapted to hold a magnetic valve assembly which when closed, stops the flow of urine, and when open, allows the urine to flow into a bell or ovoid shaped output housing. The output housing includes an output port which would be connected to the urine flow lumen below the device, which in turn is connected to a urine collection bag.

The magnetic valve assembly comprises a housing which holds a stationary magnet and a flap magnet. The lower or flap magnet is for opening and closing the urine flow path. The human body and the bladder produce an internal pressure to urge the urine fluid from the bladder. Additionally in the present urine flow control device there is additional pressure produced from the urine fluid within the length of the urine flow lumen from at least the bladder to a lower or door or flap magnet. When these pressures are less than the magnetic attraction force between the stationary magnet and the flap magnet, the flap magnet remains securely closed, blocking the flow of urine through the urine flow control device. When these pressures overcome the attractive force of the stationary magnet and the flap magnet, the flap magnet pivotally moves to an open position permitting the urine fluid to flow through the magnetic valve and into the bell or ovoid shape output housing. The stationary magnet does not move and the portion of the housing where the stationary magnet resides includes openings to permit the urine fluid to pass when the flap magnet is in the open position. When the pressures reach the critical pressure value to overcome the magnetic attraction of the stationary magnet and the flap magnet, the flap magnet hingedly opens allowing the urine fluid to flow into the bell or ovoid shaped output housing. This critical pressure value is at least the combination of the pressures described above, namely the bladder pressure and the lumen pressure.

Additional pressures that combine to make up this critical pressure may also include momentum of the flowing urine fluid through the lumen and the urine flow control device as well as any gravitational forces. The bell or ovoid shaped output housing creates additional pressure by a tornado or vortex effect of the urine fluid flowing through the output housing, which will increase the speed of the urine flow and maintain a steady downward force or pressure keeping the flap magnet open until the bladder has been efficiently voided of urine. When the bladder is voided of urine and there is no more or little urine fluid flowing, the flap valve magnet hingedly closes which prevents reflux of urine into the bladder or the upper housing of the urine control device.

Different magnet strengths may be employed to accommodate greater or lesser critical pressures to open the magnetic valve flap magnet. These critical pressures may vary from person to person and could be optimized for an individual with different bladder efficiencies and associated muscle tones.

Employing the urine control device of the invention with a catheter has the result of simulating "normal" un-catheterized urination, which would keep the bladder from shrinking, will help prevent incontinence, and will help prevent urinary tract infections when the catheter is removed.

A sample port is provided through a sidewall of the cylindrical element portion of the urine flow control device. The cylindrical element is located intermediate the input port and the input housing. This construction would allow the sterile removal of a sample of urine from the device, for various medical tests to be performed thereon.

Another aperture is provided through the sidewall of the output port. This aperture is covered by a filter which is permeable to air, but fluid resistant, which allows air to enter the urine flow control device through the sidewall of the output port. The filter has a further property of preventing urine from leaking out of the output port.

The filter covered aperture allows for pressure equalization within the flow control device and creates tiny bubbles of air (approximately 20% oxygen) that travels down the lower lumen to the collection bag. This bubble action and the biocidal effect of oxygen will prevent bio-film from forming on the interior walls of the lumen or the collection bag.

The urine control device may be manufactured as a kit with a catheter for sterility. Alternatively, the lumen of the catheter may be cut intermediate the bladder and the urine collection bag, and the top portion of the lumen would be inserted into the input port of the urine control device and the bottom portion of the lumen would be inserted into the exit port of the urine control device.

It is accordingly an object of the invention to provide a flow control device having an inlet housing, with a magnet housing disposed in the inlet housing, the magnet housing having an aperture formed therein for receiving a stationary magnet therein, the magnet housing having an annular shoulder with an annular aperture formed therein and an annular ring projecting from the annular shoulder and surrounding the annular aperture. The flap magnet is disposed at the annular shoulder and for being attracted to the stationary magnet and held against the annular ring counter to pressure of a fluid in the flow control device. The stationary magnet and the flap magnet are sized for having an attraction force set to a predetermined value, which when exceeded by the pressure of the fluid acting on the flap magnet at the annular opening results in the flap magnet pivoting away from the annular aperture at an angle while remaining at least partially in contact with the magnet housing.

In accordance with another feature of the invention, an outlet housing is affixed to the inlet housing, and the outlet housing has an outlet housing opening formed therein, a flap magnet retention device is disposed in the outlet housing opening for preventing the flap magnet from dropping and loosing contact with the magnet housing.

In accordance with yet another feature of the invention, the flap magnet retention device defines a distance to the magnet housing which limits the angle the flap magnet pivots to 45 degrees or less.

In accordance with still another feature of the invention, the magnet retention device has an inside wall, and a diameter of the flap magnet is greater than a largest distance between the inside wall and an edge of the annular aperture, such that the flap magnet cannot be positioned against the magnet housing without completely covering the annular aperture.

In accordance with yet still another feature of the invention, the outlet housing defines an annular bowl-shaped chamber leading to a drain aperture at a base of the bowl-shaped chamber, the bowl-shaped chamber having an annular wall region extending longitudinally from the drain aperture.

In accordance with another feature of the invention, the bowl-shaped chamber is free of any structures, within the annular wall region, which would disrupt a vortex flow.

In accordance with yet another feature of the invention, the annular wall region extends substantially up to the magnet retention device.

In accordance with yet still another feature of the invention, the magnet retention device has an inside wall and strips extending between opposite points on the inside wall, the strips for preventing the flap magnet from being separated from the magnet housing.

In accordance with another feature of the invention, a predetermined value is set to release the flap magnet when a pressure of 7.5-10.5 inches of $H_2O$ is realized against the flap magnet.

In accordance with yet another feature of the invention, the magnet housing has an annular rim at the aperture of the magnet housing for retaining the stationary magnet in the aperture of the magnet housing.

In accordance with another object of the invention, a magnet housing has a stationary magnet at a first longitudinal end thereof; the magnet housing has an annular aperture formed therein at a second longitudinal end of the magnet housing opposite the first longitudinal end, a flap magnet is disposed at the second longitudinal end and for being attracted to the stationary magnet and held against the magnet housing counter to pressure of a fluid acting on the flap magnet, the stationary magnet and the flap magnet are sized for having an attraction force set to a predetermined value, which when exceeded by the pressure of the fluid acting on the flap magnet at the annular aperture results in the flap magnet pivoting away from the annular aperture at an angle while remaining at least partially in contact with the magnet housing, and an outlet housing disposed at the second longitudinal end of the magnet housing, the outlet housing defining an annular bowl-shaped chamber leading to a drain aperture at a base of the bowl-shaped chamber, the bowl-shaped chamber having an annular wall region extending longitudinally from the drain aperture, the bowl-shaped chamber being free of any structures, within the wall annular region, being disruptive to a vortex flow.

In accordance to an added feature of the invention, the outlet housing has an outlet housing opening formed therein, a flap magnet retention device is disposed in the outlet housing opening for preventing the flap magnet from dropping and loosing contact with the magnet housing.

In accordance with another added feature of the invention, the magnet retention device has an inside wall, a diameter of the flap magnet is greater than a largest distance between the inside wall and an edge of the annular opening, such that the flap magnet cannot be positioned against the magnet housing without completely covering the annular aperture.

In accordance with yet an additional feature of the invention, the annular wall region extends substantially up to the magnet retention device.

In accordance with yet still an additional feature of the invention, the magnet retention device has an inside wall and strips extending between opposite points on the inside wall, the strips for preventing the flap magnet from being separated from the magnet housing.

In accordance with an additional feature of the invention, the predetermined value is set to release the flap magnet when a pressure of 7.5-10.5 inches of $H_2O$ is realized against the flap magnet.

It is yet another object of the invention to have a magnet housing having a stationary magnet at a first longitudinal end of the magnet housing, the magnet housing having an annular aperture formed therein at a second longitudinal end of the magnet housing opposite the first longitudinal end, a flap magnet disposed at the second longitudinal end and for being attracted to the stationary magnet and held against the magnet housing counter to pressure of a fluid acting on the flap magnet, the stationary magnet and the flap magnet sized for having an attraction force set to a predetermined value, which when exceeded by the pressure of the fluid acting on the flap magnet at the annular aperture, results in the flap magnet pivoting away from the annular aperture at an angle while remaining at least partially in contact with the magnet housing.

BRIEF DESCRIPTION OF THE DRAWINGS

FIG. 2A is a side view of the upper portion of the urine control device including the input port and the upper housing.

FIG. 2B is a sectional view taken along lines 2B-2B of FIG. 2A.

DETAILED DESCRIPTION OF THE PREFERRED EMBODIMENT

Figure 1:
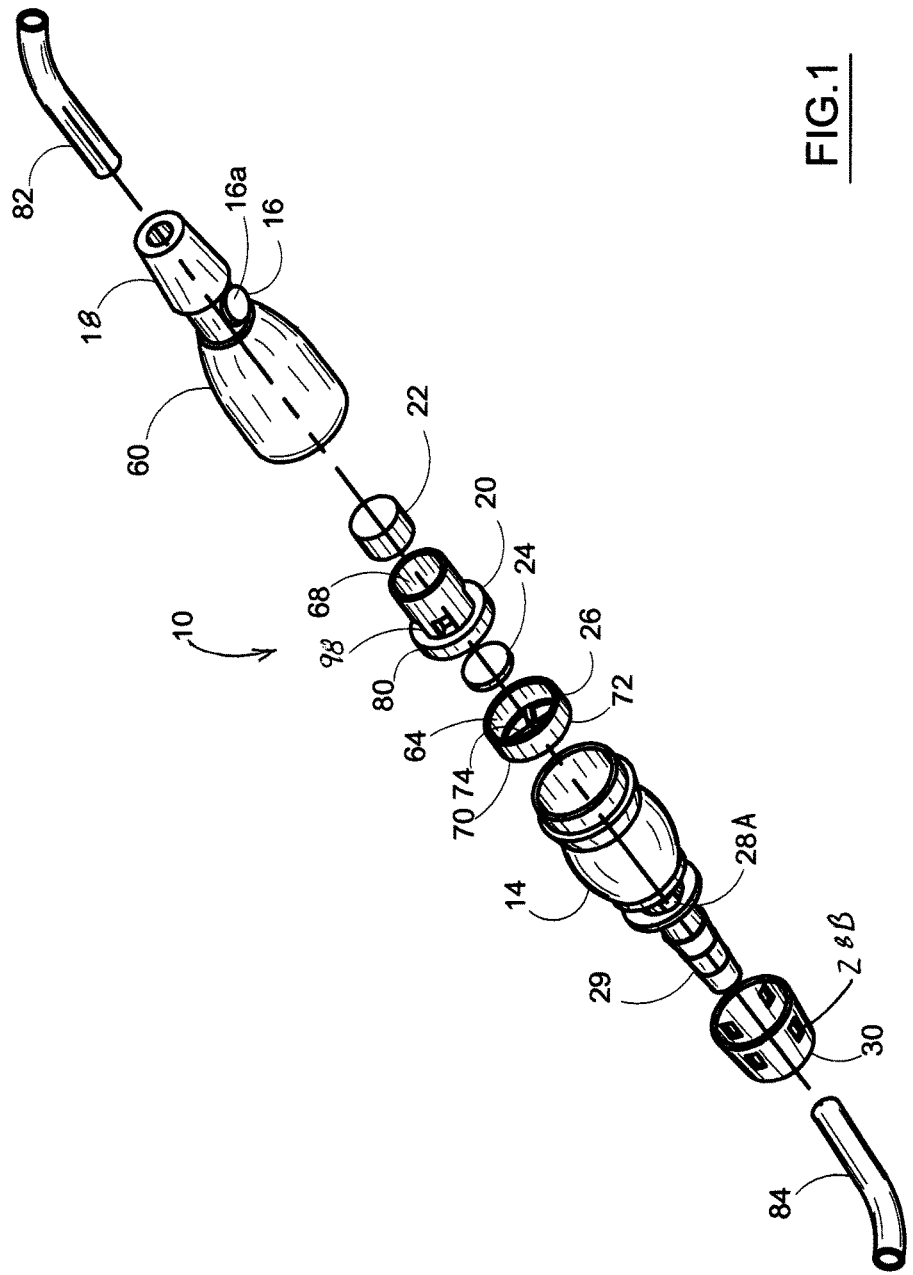
FIG. 1 is an exploded view of the urine control device of the invention.
Figure 6:
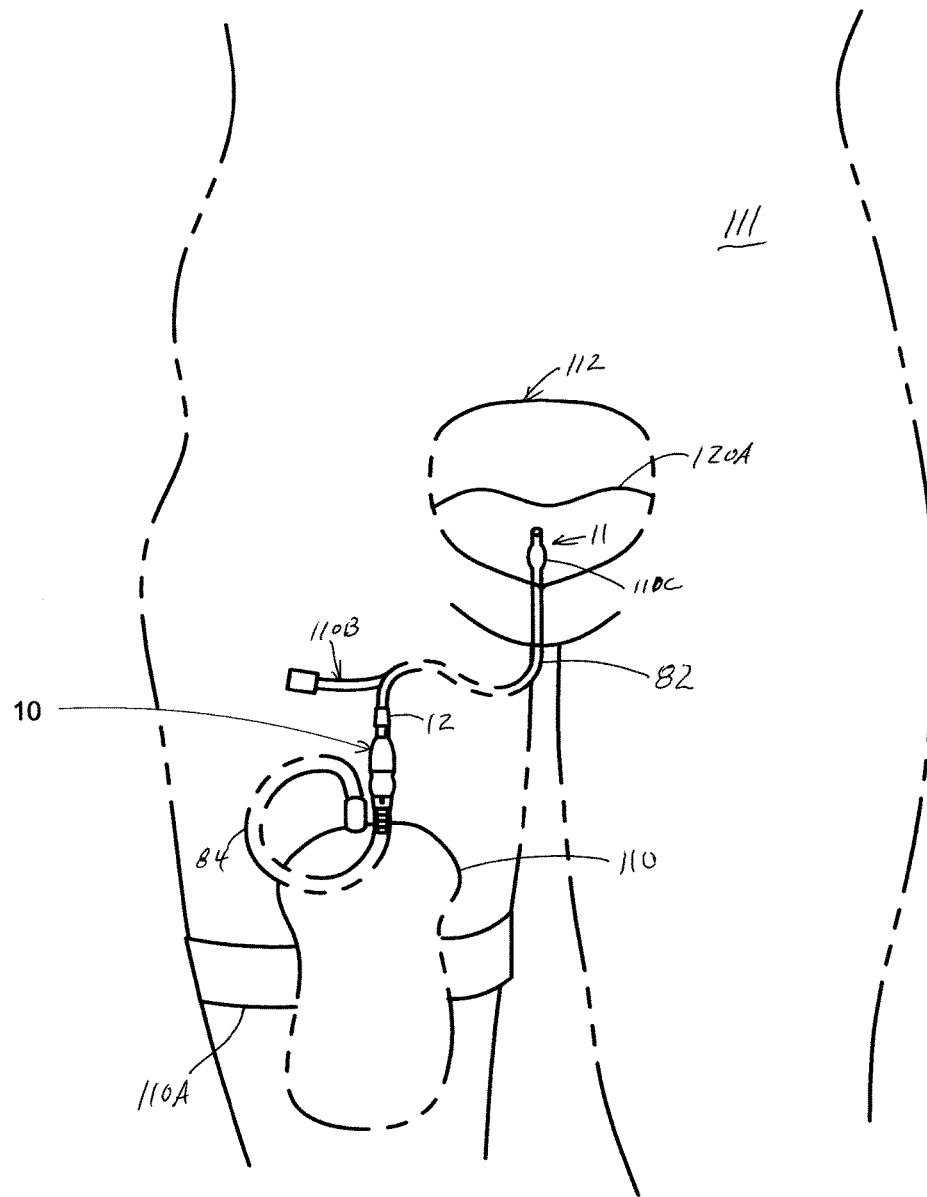
FIG. 6 is a view of the urine control device placed in line with the urine flow lumen from a catheter intermediate the bladder and the urine collection bag.

Referring now specifically to FIG. 1, an exploded view of the urine control device 10 to be employed downstream of a catheter, such as a Foley catheter 11 that has been inserted into the bladder 112 of a patient 111 as shown in FIG. 6. The urine control device 10 includes an upper or first lumen 82 which connects to the Foley catheter 11 and forms a passageway to receive urine fluid 120A from the bladder 112. The lumen 82 is connected to an input port 12 of the urine control device 10. In some embodiments, a sterile input port cover 18 is adapted to be fit atop the barbed input port 12 to keep the barbed input port 12 clean. The sterile input port cover 18 is removed and the upper lumen 82 frictionally interfits onto a central aperture 13 on the top of input port 12. A lower or second lumen 84 is frictionally secured onto a barbed exit port 29 of the urine control device 10 and a locking cap microport cover 30 may secure the lumen 84 thereon.

In other embodiments, a kit would be formed with the Foley catheter 11, and the first lumen 82 may already be secured in the input port 12 and the second lumen 84 may also already be secured to the exit of the barbed exit port 29.

Figure 8A:
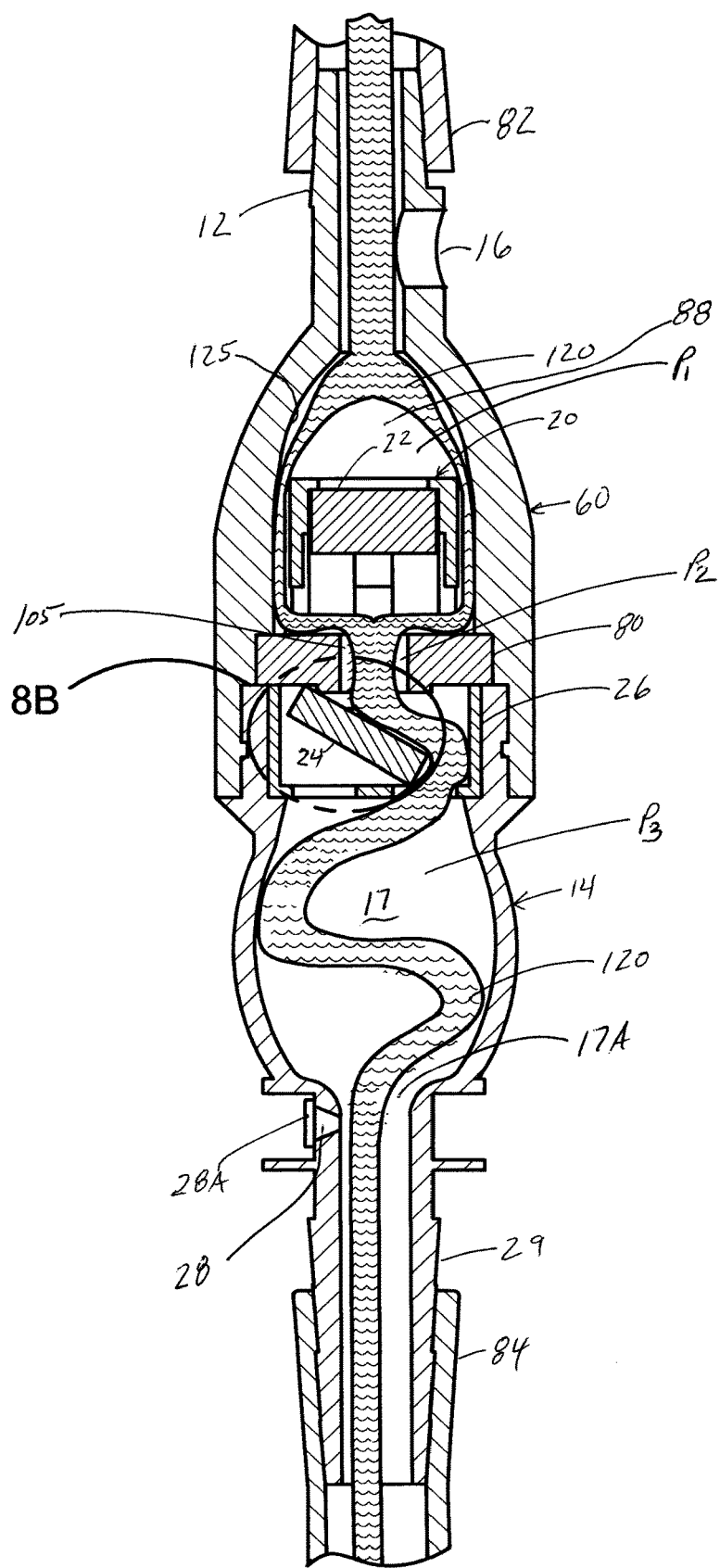
FIG. 8A is a sectional view of the urine control device with the flap magnet in an open position, showing representative urine fluid flow through the entire urine flow control device from the upper urine flow lumen to the lower exit housing and then to the lower urine flow lumen. The flow of urine with a vortex effect is seen in the lower housing.

First lumen 82 forms the beginning of a central passageway 86 for urine fluid 120A to flow through the entire length of the urine control device 10. The flow of the urine fluid 120A is shown in FIG. 8A. The second lumen 84 completes the central passageway 86 from the urine control device 10 to the urine collection bag 110.

Depending from the bottom of the input port 12 is a detent cylindrical element 62 having a cylindrical sidewall 63. Cylindrical element 62 includes the central passageway 86. A sampling port 16 is provided through the cylindrical sidewall 63 of the cylindrical element 62 to provide access to the central passageway 86 and to the urine fluid 120A therein. Sampling port 16 has a self sealing silicone plug 16A to provide access for a sample of urine when required.

Figure 3:
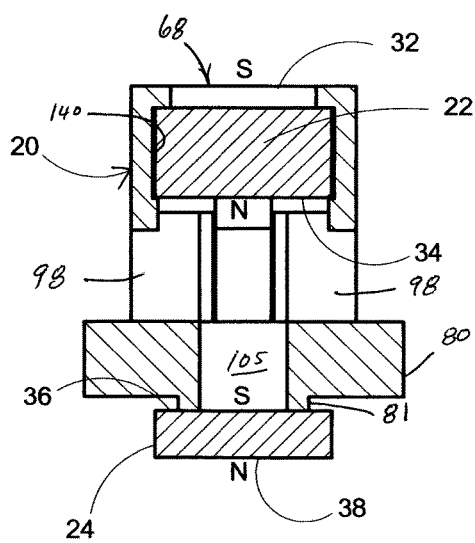
FIG. 3 is a sectional view of the magnet housing of the urine control device with the lower magnet in the closed position.
Figure 4:
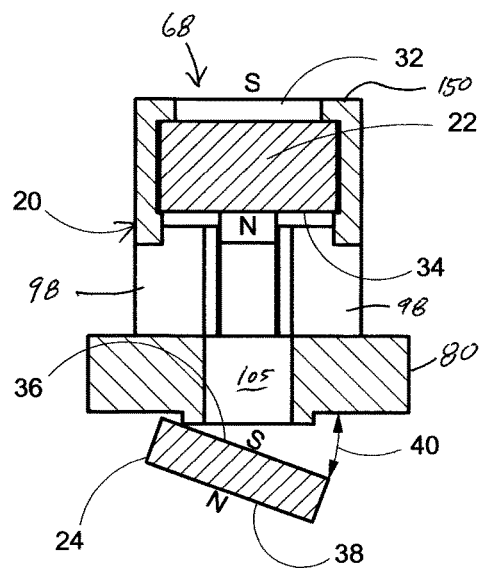
FIG. 4 is a sectional view of the magnet housing of the urine control device with the lower magnet in the open position.
Figures 5A, 5B:
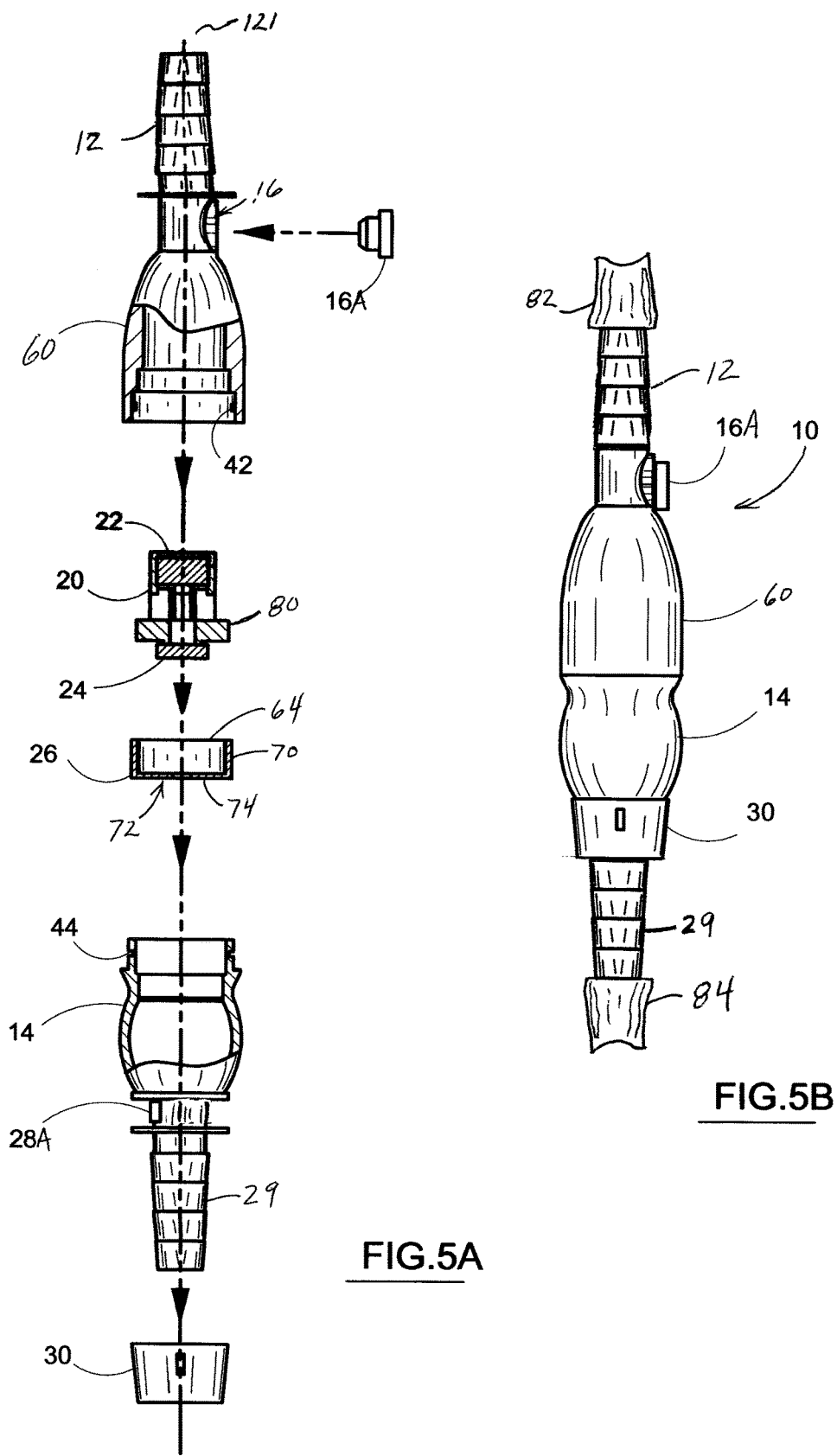
FIG. 5A is an exploded partial section and cutaway view of some of the components of the urine control device.
FIG. 5B is a side view of the outside of the assembled urine control device.

Directly below and integral with the cylindrical element 62 is the upper, or inlet or first housing 60 and an attachable lower, outlet or second housing 14. Therewithin, magnet housing 20 is supported within first housing 60 by a friction fit. Referring to FIGS. 3 and 4, magnet housing 20 includes a top aperture 68 to receive stationary magnet 22 securely therein. Stationary magnet 22 is press fit into aperture 68 and therefore is fixed in aperture 68 and does not move. To further secure stationary magnet 22, an inwardly facing radial lip 150 is provided about the upper circular perimeter of the aperture 68. As best seen in FIG. 1 and FIG. 5A, a flap magnet retention device 26 forms a lower boundary for the movable flap magnet 24 in a region at the bottom of the magnet housing 20. The lower magnet retention device 26 has a top opening 64, a cylindrical sidewall 70, a bottom opening 72, and a pair of perpendicular narrow strips 74. The pair of perpendicular narrow strips 74 are located at the bottom opening 72 and are connected to the cylindrical sidewall 70 forming a barrier for flap magnet 24. This barrier formed by strips 74 prevents the flap magnet 24 from exiting magnet retention device 26. The strips 74 of retention device 26 also serve to limit the angle of the opening of flap magnet 24, and prevent flap magnet 24 from moving into the bowl or chamber 17 of the second housing 14 except within retention device 26. Preferably, an interior height 27A of retention device 26 is not greater than approximately the diameter of lower magnet 24.

The first housing 60 and the exit second housing 14 are preferably manufactured from K-Resin® (a registered U.S. trademark of Chevron Phillips Chemical Company LP Ltd. of Woodlands, Tex.), a polycarbonate, which has a material property of being transparent. Other materials may be employed provided they have the required material properties.

The magnet housing 20 is preferably manufactured from silicone. This would include medical grade silicone which has a hardness value of 4 (+/−) 1 SHORE A as measured on a durometer. This gives a range of about 3-5 SHORE A. Other materials may be employed provided they have the required material properties.

In this discussion, and best seen in FIG. 8A, the urine fluid flow 120 is shown passing through the urine flow control device 10. The urine fluid flow 120 shows the flow path of urine fluid 120A through the urine flow control device 10.

Figure 9:
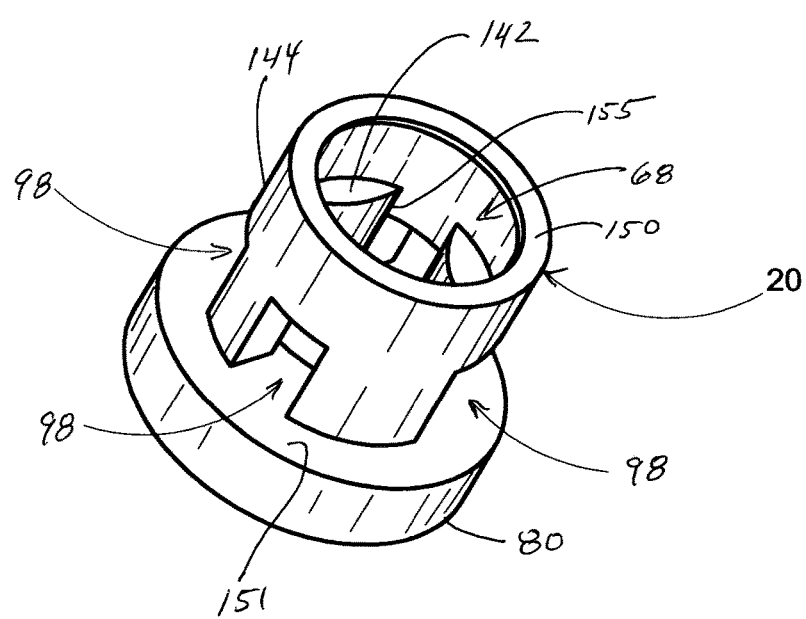
FIG. 9 is a perspective view of the magnet housing of the urine control device showing the plurality of openings for the urine fluid to flow by the stationary magnet towards the lower flap magnet.

The magnet housing 20, includes a rim or annular shoulder 80. Magnet housing 20 fits within first housing 60 such that should 80 fits into chamber 88 and against inner wall 88A within diameter D2. Shoulder 80 is dimensioned appropriately such that the height of shoulder 80 is slightly greater than wall 88A such that when second housing 14 is interfit into first housing 60 shoulder 80 will be compressed to create a compression seal against the top edge 77 of magnet retention device 26 and against top edge 15 of second housing 14. The bottom central portion of shoulder 80 includes a flat annular ring 81. Above the shoulder 80 are four openings 98 which pass through the outer sidewall 144 of the magnet housing 20 as shown in FIGS. 9 and 10A. The openings 98 must be sufficiently large to permit struvite crystals or other stones or crystals which be entrained in the urine fluid flow 120 to pass through the openings 98. By making the openings 98 large enough, blockage by the struvite crystals or other material that may be entrained in the urine fluid flow 120 is prevented.

Figure 12:
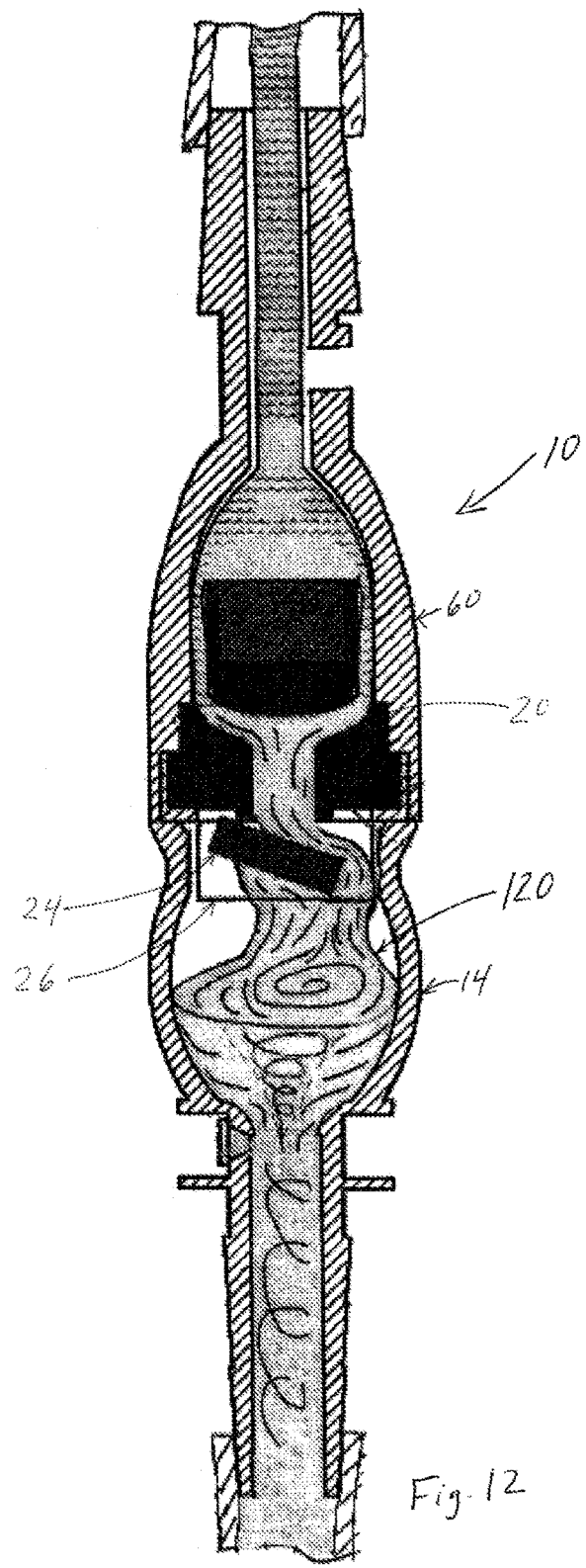
FIG. 12 is a section view of the catheter to show the vortex flow of fluid in the bowl-shaped chamber.

When flap magnet 24 is in the open position as shown if FIG. 4 and FIG. 8A, urine fluid 120 will flow though the four openings 98, through aperture 105, over flap magnet 22 and into the second housing 14 which has an ovoid internal shape, in a swirling action. This swirling action of the urine fluid flow 120A is shown in FIG. 8A and FIG. 12. In FIG. 8A the vortex flow is created and is shown with a portion of the urine fluid 120A shown in a vortex as the urine fluid 120 flows from above and against flap magnet 24 into and through the interior bowl-shaped chamber 17 of second housing 14 leading to a drain aperture 17A at the base of chamber 17. Chamber 17 includes an internal annular wall region 17B extending from the drain aperture 17A towards the magnet retention device 26. Also see FIG. 7A. FIG. 8A shows a symbolic portion of the urine flow 120 in second housing 14 to illustrate the vortex, swirling or tornado effect within chamber 17. This effect is based on Bernoulli's principles that for an inviscid fluid (ideal fluid with no viscosity) flow, an increase of speed of the fluid occurs simultaneously with a decrease of pressure. Thus, when the internal body pressure of the bladder 112 and the urine flow 120 reaches a pressure in the range of 7.5-10.5 inches of $H_2O$, flap magnet 24 releases in a hinging motion directing the urine fluid flow 120 into a direction which will optimize the direction and flow of urine 120A such that the increased speed of the urine flow 120 will cause flap magnet 24 to remain in an open position until the magnetic attraction between stationary magnet 22 and flap magnet 24 reaches a level that the flap magnet 24 will close because of the greater attraction of stationary magnet 22. As a result, the direction of the hinged flap magnet 24, with Bernoulli's principal of the fluid flow 120, will develop a tornado effect within chamber 17 with the urine flow 120 which will increase the speed of the urine flow 120 and maintain a steady downward force keeping the flap magnet 24 open until the bladder 112 has been efficiently voided of urine 120.

It is noted that bowl-shaped chamber 17 as shown preferably has relatively smooth internal walls, an annular wall region extending longitudinally from the drain aperture 17A, and the bowl-shaped chamber is free of any structures, within the annular wall region that would be disruptive to a vortex flow Further, chamber 17 would not include any internal structure that would disrupt or inhibit a vortex flow.

In a working example, the distance between the stationary magnet 22 and flap magnet 24 is 0.630 inches +0.005/−0.000 inches. The Gauss strength of the stationary magnet 22 is 1225.0 +/−10.0 Gauss. The Gauss strength of the flap magnet 24 is 635.0 +/−15.0 Gauss. The pressure of the liquid to open the flap magnet 24 is 7.5 -10.5 inches/$H_2O$. The amount of the surface area of the flap magnet subject to pressure is $A=(Pi)(r^2)$. The diameter of the opening 105 is 0.201 inches, the radius of the opening 105 is 0.1005 inches.

The stationary magnet 22 and the flap magnet 24 are oriented in such a fashion that the magnetic fields attract. It is well known that magnets have poles, one positive or north, designated by (N) and one negative or south, designated by (S). The stationary magnet 22 may have a bottom portion 34 which is north (N) and a top portion 32 which is south (S). In this arrangement, the flap magnet 24 will have a top portion 36 which is south (S) and a bottom portion 38 which is north (N). This arrangement is best seen in FIGS. 3 and 4.

Alternatively, the stationary magnet 22 may have a bottom portion 34 which is south (S) and a top portion 32 which is north (N). In this case, the flap magnet 24 must have a top portion 36 which is north (N) and a bottom portion 38 which is south (S). This alternative embodiment is not shown in the FIGS. 3 and 4.

In either of these magnet arrangements, the flap magnet 24 is attracted to the stationary magnet 22. Both the flap magnet 24 and the stationary magnet 22 are generally cylindrical with a diameter and height. The stationary magnet 22 and the flap magnet 24 may be of different or have generally the same diameter; however, generally the height of the stationary magnet 22 is greater than the flap magnet 24.

Figure 8B:
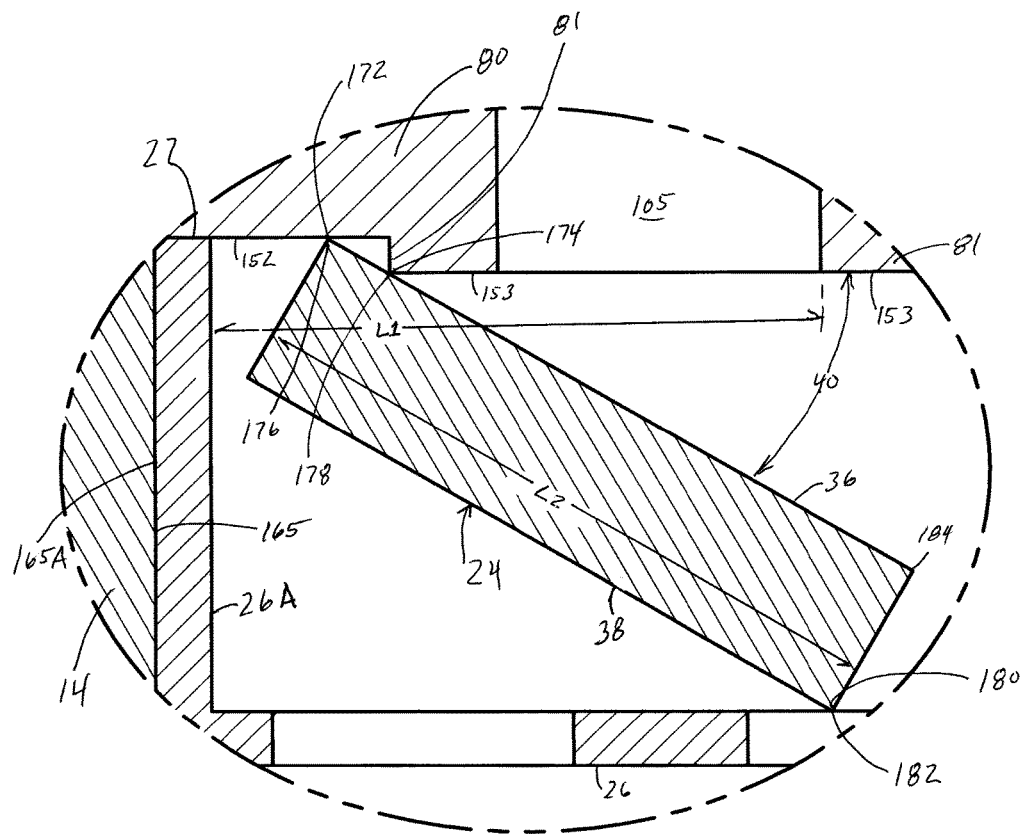
FIG. 8B is a close up view of the portion of the urine control device shown in the circled area of FIG. 8A.

The diameter or length L2 of the flap magnet 24 is chosen to be greater than the distance L1 formed starting from the inner sidewall 26A of the magnet retention device 26 to the far side of aperture formed by the bottom of the central urine passageway 105. This is best seen in FIG. 8B. In the event that flap magnet 24 gets loose, it will always close having sufficient diameter L2 to completely arrest the urine fluid flow through the central urine passageway 105.

In a working example, stationary magnet 22 has a diameter of 0.361 inches and a height of 0.253 inches and has a Gauss value of about 1225.00 (+/−) 10.0 with the north side of the stationary magnet 22 in the towards input port 12 The flap magnet 24 has a diameter of 0.375 inches and a height of 0.091 inches and a Gauss value of about 635.00 (+/−) 15.0 with the same orientation of north as the stationary magnet 22. When the pressure in the first housing 60 reaches about 7.5 to 10.5 inches of $H_2O$ [pure water at 4 degrees Centigrade], the flap magnet 24 opens in a hinge like action. The opening of the flap magnet 24 is in response to sufficient pressure bearing down on the top 36 of the flap magnet 24 through aperture 105.

When the flap magnet 24 is in an open position, it directs the urine fluid flow 120 in a specific direction into the chamber 17 of second housing 14 which starts the vortex action. This is because the flap magnet 24 hingedly opens and the urine fluid flow 120 is directed against and over flap magnet 24 to one side and downward into the chamber 17 of second housing 14. Through action of Bernoulli forces, the chamber 17 of second housing 14 has a lower internal pressure than the pressure in chamber 88 of first housing 60 drawing the urine fluid 120A into the second housing 14. The internal shape of chamber 17 of second housing 14 combined with the lower pressure in chamber 17 induces the urine fluid flow 120 to move in a vortex or swirling motion as it passes over and against flap magnet 24 and into the chamber 17 and through second housing 14 to the drain aperture 17A. The combination of the lower pressure, the induced vortex, and the directional flow over the flap magnet 24 when flap magnet 24 is in the open position aids in draining the urine fluid 120A more completely from device 10 and the bladder 112. This aids in removing the old, rancid, possibly infected urine fluid 120A which may remain in the bladder 112 when using a prior art conventional continuous flow catheter.

This magnetic attraction between the stationary magnet 22 and flap magnet 24 holds the flap magnet 24 magnetically to the bottom side of shoulder 80 and to annular ring 81. When flap magnet 24 is in a closed position, it blocks and prevents the urine fluid flow 120 through the passageway 86 and through aperture 105 towards the second housing 14. As shown in FIG. 3 the flap magnet 24 top portion 36 is in a closed position below central valve urine passageway 105 of shoulder 80. However, the flap magnet 24 will move to an open position when the critical pressures exceed the magnetic attraction between the stationary magnet 22 and the flap magnet 24. Due to the magnetic field lines between the stationary magnet 22 and the flap magnet 24, when the flap magnet 24 opens, the flap magnet 24 moves in an angular fashion creating an opening at aperture 105 which opens passageway 86 allowing urine fluid flow 120 to continue within passageway 86 below the position of flap magnet 24. When the critical pressure overcomes the magnetic attraction threshold between the stationary magnet 22 and the flap magnet 24, the flap magnet 24 opens angularly as shown in FIG. 4. The maximum open position of flap magnet 24 will be until flap magnet 24 rests against one or more of the perpendicular narrow strips 74 of the lower magnet retention device 26.

The ability of the flap magnet 24 to open in an angular fashion is attributed to the arrangement of the fixed, unmovable stationary magnet 22 with respect to the angularly movable flap magnet 24. In this arrangement magnetic fields are generated by the stationary magnet 22 which attract, support and hold the flap magnet 24 against the shoulder 80 and lip 81. Additionally the flap magnet 24 generates magnetic fields which attract the stationary magnet 22. When the critical pressure is greater than, and thus overcomes, the attractive forces between the upper stationary magnet 22 and the movable flap magnet 24 then the lower stationary magnet 24 is angularly displaced until at a maximum, a portion of flap magnet 24 rests on the lower magnet retention device 26. Due to micro-discontinuities and uneven magnetic fields generated and interacting between the stationary magnet 22 and the movable flap magnet 24, the movable flap magnet 24 will move downward in an angular fashion, with one part of the top portion 36 of the movable flap magnet 24 resting against lip 81 of shoulder 80 or magnetically closely attracted to shoulder 80 and lip 81. The bottom portion 38 of flap magnet 24 is towards or resting against the magnet retention device 26.

The silicone magnetic housing 20 frictionally interfits into the upper housing 60. Upper housing 60 rotatably attaches the lower housing 14 to the upper housing 60 securing the magnet housing 20 by a barb 42 located on the interior of the upper housing 60 which fits into a groove 44 located in the lower housing 14. When the barb 42 is rotated in the groove 44 the upper housing 60 is secured to the lower housing 14.

Lower housing 14 has a generally ovoid shaped inner chamber 88. Depending from the bottom of the lower housing 14 is a barbed exit port 29 to receive lumen 84. A microport hole 28 passes through the sidewall of the barbed exit port 29. The microport hole 28 allows atmospheric air to enter the passageway 86. The microport hole 28 is covered by a microfilter covering 28A, which attaches by adhesive or is frictionally held to the sidewall of barbed exit port 29 to cover hole 28. FIG. 5A shows three of the four microport holes 28 which provide a passageway for entry of the atmospheric air through the microport holes 28. Holes 28 covered with microport covering 28A allow air into passageway 86 but do not allow fluid flow 120 to exit through hole 28. Hole 28 allows for pressure equalization in the device 10 and create tiny cleansing bubbles of air that travel down the passageway 86 to the collection bag 110. Cover 30 has for openings 28B to allow atmospheric communication to hole 28. This introduction of atmospheric air which contains approximately twenty percent (20%) oxygen is biocidal to many microorganisms. The atmospheric oxygen which enters through the microfilter covering 28A and into the microport hole 28 flows into passageway 86 and into lumen 84. Lumen 84 forms the remainder of passageway 86 and the urine fluid flow 120 continues along passageway 86 to the urine collection bag 110. The biocidal properties of the oxygen entering through the microport hole 28 prevents bio-film from forming on the interior passageway 86, of the second lumen 84 and the interior of the collection bag 110. The bio-film formation is arrested due to the fact that the gaseous oxygen kills the microorganisms. This helps prevent reflux and microbiological contamination of the urine flow control device 10 and the associated catheter and urine collection bag 110. By preventing such reflux, urinary tract infections are reduced.

Referring now specifically to FIG. 2A, a plan view of the upper portion of the urine control device 10 including the barbed input port 12 and the upper housing 60 is shown. A cylindrical element 62 is shown intermediate the barbed input port 12 and the upper housing 60. A silicone plug 16A is shown passing through the sidewall of the cylindrical element 62. The self sealing silicone plug 16A, permits access to take a sample of the urine fluid 120A that comes from the patient for any medical tests that may be required.

Referring now specifically to FIG. 2B. a cut-away view taken along lines 2B-2B of FIG. 2A with the silicone cylindrical plug 16A not in place. A central aperture 13 on the top of barbed input port 12 is designed to receive the first lumen 82 of the catheter therein. A central passageway 86 passes through the center of the barbed input port 12 and then into the center of cylindrical element 62 and then into the generally bell shaped upper portion chamber 88 of the input or first housing 60. Two barbs 42 are located at the bottom 90 of the upper housing 60, along the interior sidewall 88B.

A sample port 16 passes through the sidewall 63 of the cylindrical element 62 allows sampling of urine fluid 120A passing through the central passageway 86. The upper portion chamber 88 of the interior of the upper housing 60 is bell shaped and expands to a maximum diameter D1. Below the bell shaped upper housing 60 is an interior cylindrical inner sidewall 88A with a diameter D2 which is somewhat larger than diameter D1. Immediately below the interior cylindrical portion sidewall 88A with a diameter of D2 is second cylindrical shoulder portion inner sidewall 88B with a diameter D3. Diameter D3 is somewhat larger than diameter D2. The internally disposed barbs 42 are located on inner sidewall 88B, on the portion of the interior upper housing 60 which has diameter D3. The reason for the staggered diameters of the interior of the upper housing 60 is so that it may receive the magnet housing 20 therein such that annular shoulder 80 fits within and is frictionally held in place by wall 88A. Once the magnet housing 20 is in place, the lower housing 14 is interfit into the bottom 90 of the first housing 60, where the barbs 42 fit into a groove 44, which when rotated, lockably secures the upper housing 60 to the lower housing 14 and the top of second housing 14 has a compression fit against shoulder 80 of magnet housing 20 to form a leak free fit.

Referring now specifically to FIG. 3, the magnet housing 20 of urine control device 10 is shown with flap magnet 24 in the closed position. The magnet housing 20 is interfit inside the upper housing 60. Stationary magnet 22 is interfit into aperture 68. Stationary magnet housing 20 includes an interior cylindrical sidewall 140 with columns 155. The columns having a top 142. The stationary magnet 22 fits into the opening formed by the cylindrical sidewall 140 and rests on surface 142. FIG. 3 also shows the top portion 32 of the stationary magnet 22 being of a south (S) polarity and the bottom side 34 of the stationary magnet 22 being of a north (N) polarity. Additionally, FIG. 3 shows several of the urine passageways 98 in the magnet housing 20 above shoulder 80 which lead to a central valve urine passageway 105. Central valve urine passageway 105 is part of central passageway 86 and provides the opening for the urine flow 120 from above the magnet housing 20 through magnet housing 20 when the flap magnet 24 is in the open position as shown in FIG. 4. In FIG. 4, magnet 24 is shown displaced by the angle 40. This angle is preferably 30 degrees to 45 degrees.

In FIG. 4, the weight and pressure of the urine flow 120 from the bladder causes the flap magnet 24 to angularly displace, the displacement angle shown at 40 allowing the urine to flow to the lower housing 14 where it then flows to the urine collection bag 110. The urine flow 120 through the urine control device 10 will be best seen in FIG. 5A and FIG. 8A, where the direction of flow is indicated by arrows and line 121 in FIG. 5A.

Figure 7A:
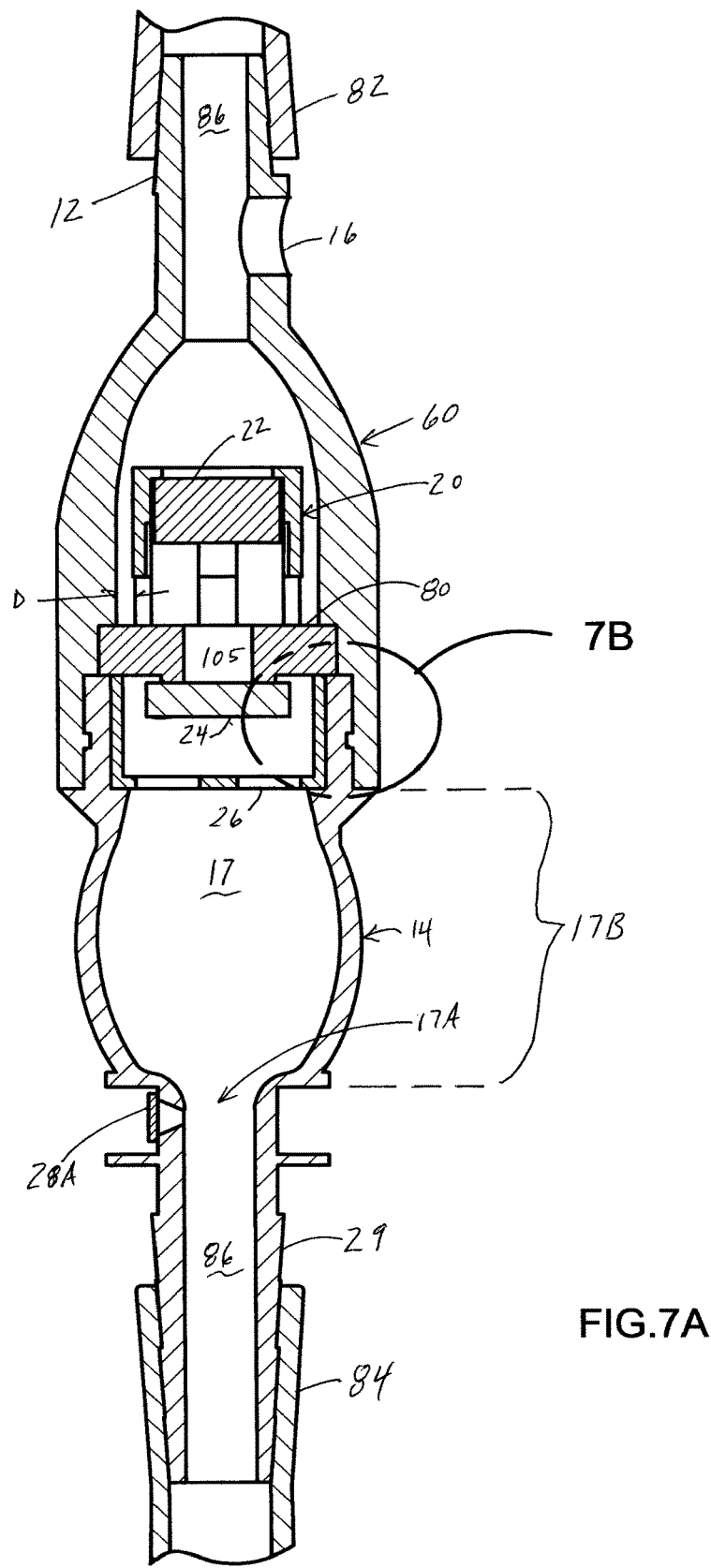
FIG. 7A is a sectional view of the urine control device with the flap magnet in the closed position.

At the bottom of the second housing 14 is at least one micropore hole 28 which is seen best in FIG. 7A. The microport hole 28 is covered by a microport filter 28A which may be attached with an adhesive and permits outside air to enter the urine stream through microport hole 28 while not permitting the urine stream from leaving the urine control device 10. Such micro filter 28A is manufactured by TAPESPEC® of New Zealand. A microport cover 30 covers the micropore hole 28 and microport filter adhesive 28A when desired which is shown in FIG. 1. The air introduced into the urine flow 120 is approximately 20% oxygen which is a highly toxic gas for many types of microorganisms. The oxygen is quite lethal and creates a hostile environment which kills many microorganisms in the second lumen 84 and urine retention bag 110. This prevents or minimizes the possibility of infection of the patient and extends the length of time before the urine retention bag 110 would need to be replaced.

Referring specifically to FIG. 5B a plan view of the urine control device 10 is shown assembled. The first housing 60 is shown connected to the second housing 14. Once the sterile input cover 18 is removed, the upper lumen 82 is fit over the barbed input port 12. The microport cover 30 is affixed over the barbed exit port 29.

Referring specifically now to FIG. 6, a view of the urine control device 10 placed in line with the first lumen 82 of a catheter which has been inserted into the bladder 112 of the patient 111 and a second lumen 84 connected to a urine collection bag 110 is shown. This is generally how the urine control device 10 is employed with a Foley catheter 11 inserted into a patient 111. The catheter 11 drains the urine fluid 120A from the bladder 112 to the urine flow control device 10. In many cases, but not all, the urine storage bag 110 may be attached to a leg by a band 110A. A Luer Lock connector 110B allows air to fill a balloon 110C once the Foley catheter 11 is inserted into the bladder 112. When the balloon 110C is inflated the catheter 11 will remain in the bladder 112.

Referring now specifically to FIG. 7A a sectional view of the urine control device 10 with the flap magnet 24 in the closed position, preventing any urine flow 120 from the bladder and above second magnet 24. Central passageway 86 provides a channel for urine flow 120. Flap magnet 24 is held against a flat annular ring 81 by the magnetic attraction between first magnet 22 and flap magnet 24. The diameter of the flap magnet 24 is chosen to be such that when flap magnet 24 is in a closed position within magnet retention device 26, the central urine passageway 105 through the flat annular ring 81 will be completely blocked and sealed by flap magnet 24. Annular ring 81 prevents the top 36 of the flap magnet 24 from becoming vacuum locked against shoulder 80.

Figure 7B:
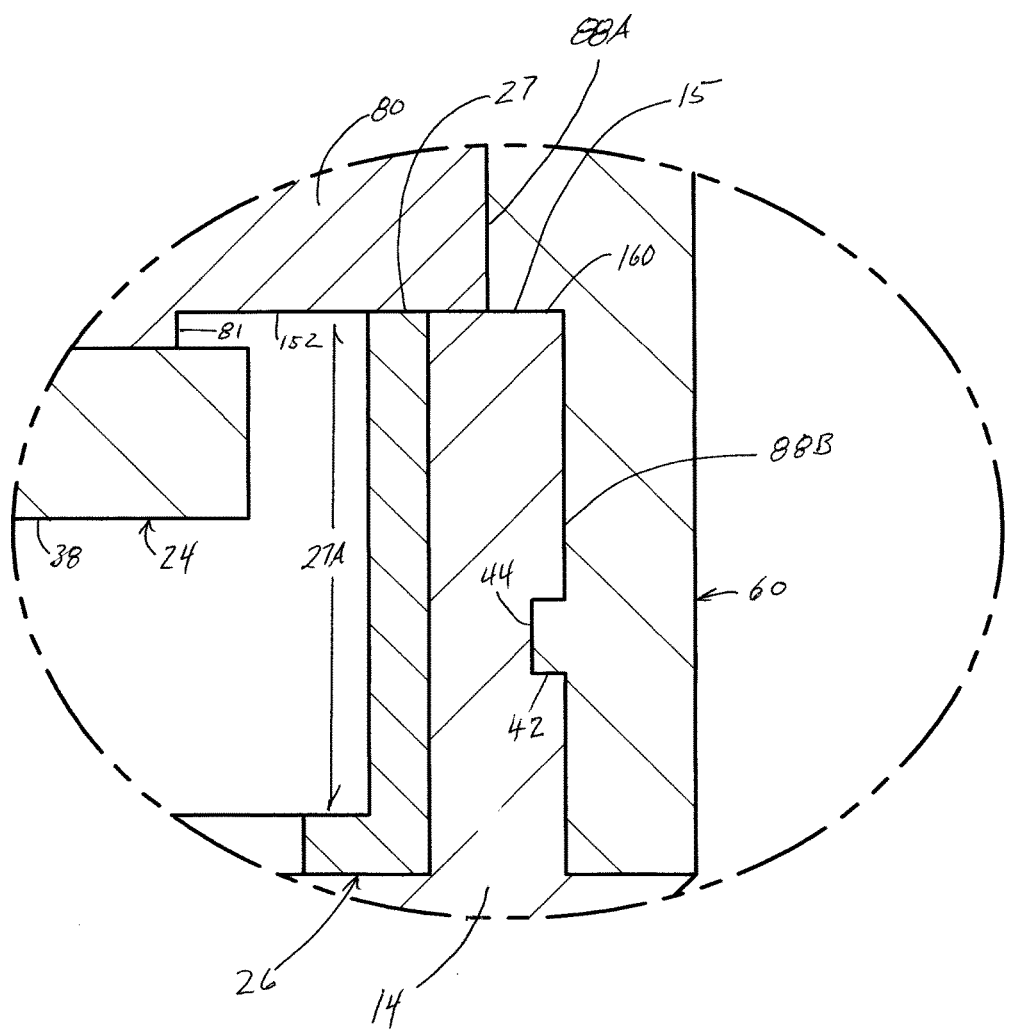
FIG. 7B is a close up view of the portion of the urine control device shown in the circled area of FIG. 7A.

FIG. 7B is an enlarged view of the portion of the urine control device 10 shown in the circled area of FIG. 7A. FIG. 7B shows the spatial arrangements of a portion of the annular shoulder 80, the annular ring 81, the flap magnet 24 in a closed position, the bottom 152 of the annular shoulder 80, the intersection of the top 27 of the magnet retention device 26 with the bottom 152 of the annular shoulder 80, the intersection of the top 15 of second housing 14, with both the bottom 152 of the annular shoulder 80 and the step down 160 between the inner sidewall 88A and interior sidewall 88B. Annular shoulder 80 extends a small distance below inner wall 88A. Shoulder 80 is made of medical grade silicon or equivalent and both the magnet retention device 26 and the second housing 14 are made from a polycarbonate of a K resin type or equivalent. The medical grade silicon forms an elastic compression gasket 162 at the point of the compression of shoulder 80 by the top 15 of second housing 14 and the top 27 of retention device 26. This elastic compression gasket 162 seals the intersection of element 15 and element 152 averting the possibility that any urine fluid 120A may escape. In FIG. 7B, the compression gasket is shown in a compressed state.

Barb 42 is shown locked in groove 44 preferably forming a one-time connection between the first housing 60 and the second housing 14. The urine flow control device 10 is designed for a one time use, not to be reused. If the first housing 60 and the second housing 14 are forced open, the barb 42 would fracture and it would not be possible to put the first housing 60 and the second housing 14 together again.

Referring now specifically to FIG. 8A a sectional view of the urine control device 10 with the flap magnet 24 being forced to an open position by the pressure and the weight of the urine in the bladder 112 and the first lumen 82, allowing the urine to flow to the second housing 14, to the second lumen 84, and then to the urine collection bag 110. The flap magnet 24 is hingedly displaced in an angular fashion, and is shown as the angle designated by the curved line 40 in FIG. 4.

Flap magnet 24 opens angularly as indicated by the curved line shown at element 40. The angle may vary to any angle within the range of above zero degrees to about 60 degrees where it is stopped by the lower magnetic retention device 26.

The momentum of the urine flow 120 along the passageway 86 is caused by the pressure exerted by the bladder 112, the weight of the urine fluid 120A itself, and the velocity of the urine fluid 120A in the urine flow 120. When the momentum of the urine fluid 120A in the urine flow 120 falls below a critical level, the flap magnet 24 moves angularly back to the closed position, closing off the urine flow 120 in the passageway 86 and the central urine passageway 105 through the center of the shoulder 80.

The urine flow 120 starts in the bladder 112 and proceeds through the first lumen 82 to the top of the urine control device 10. The urine flow 120 exits the first lumen 82 into the upper part of the urine control device 10 where it enters a central passageway 86 and proceeds into the inside of the bell shaped first housing 60. The central passageway 86 is the passageway for the urine flow 120 which passes through the urine control device 10. Inside the bell shaped input housing 60 is the magnet housing 20. The flap magnet 24 blocks the urine flow 120 and causes the urine flow 120 to move to the region intermediate the inner sidewalls 125 of the bell shaped input housing 60 and the area where the magnet housing begins. This allows the urine flow 120 to flow about the magnet housing 20. This opening between the inner sidewalls 125 of the bell shaped input housing 60 and the outer sidewalls 144 of the magnet housing 20 is part of the passageway 86 and provides for the urine flow 120 down the outer sidewalls 144 of the magnet housing 20 until the urine 120 reaches the shoulder 80. A distance D seen in FIG. 3 exists between the outer sidewall 144 of the magnet housing 20 and the inner sidewall 125 of housing 60.

Above the shoulder 80 are the outer sidewalls 144 of the magnet housing 20 showing the four openings 98 which connect to the central urine passageway 105 which is best seen in FIG. 9. Located on the interior side of the interior cylindrical sidewall 140 are a plurality of vertically oriented shoulders 155. These act as a bottom support for the stationary magnet 22. The stationary magnet 22 bottom portion 34 rests upon the top 142 of the aforementioned shoulders 155. This, in combination with the stationary magnet securing lip 150 keeps the stationary magnet 22 in place and stationary.

At the bottom of the outer sidewalls 144 of the magnet housing 20 there are four openings 98. The urine flow 120 enters the four urine passageway openings 98 located above the shoulder 80 which lead to a central urine passageway 105, which allows the urine flow 120 to pass from the upper housing 60 through the passageway 105 to the top portion 36 of the flap magnet 24. At this point, the forces of the magnetic attraction between the stationary magnet 22 and the flap magnet 24 are opposed by the weight of the urine 120, the force of pressure of the urine from the bladder, and any momentum from the urine flow 120. When the force of the urine in the urine flow 120 overcomes the magnetic attraction force between the stationary magnet 22 and the flap magnet 24 the urine will cause flap magnet 24 to move angularly downward to an open position. At this point the urine flow 120 is through the central urine passageway 105 back to the central passageway 86 into the ovoid shaped lower exit housing 14. The urine flow 120 takes on a vortex or tornadic path into and inside the ovoid shaped or bowl-shaped chamber 17 of second housing 14. This vortex or tornadic path inside the chamber 17 of second housing 14 creates a low pressure area within chamber 17, lower pressure than in first housing 60 which increases the velocity and momentum of the urine flow 120 along the passageway 86 helping to empty the bladder 112 more completely. The urine flow 120 then enters the hollow center of the barbed exit port 29 where it is connected with the second lumen 84 and finally the urine flow 120 discharges into the urine collection bag 110 after the bladder 112 has been emptied.

FIG. 8B is an enlarged up view of the portion of the urine control device shown in the circled area of FIG. 8A. FIG. 8B shows the spatial arrangements of a portion of the annular shoulder 80, the annular ring 81, the flap magnet 24 in an open position, the bottom 152 of the annular shoulder 80, the bottom 153 of annular ring 81 the intersection of the top 27 of the flap magnet retention device 26 with the bottom 152 of the annular shoulder 80, the point of contact of outer wall 165 of the flap magnet retention device 26 and the inner wall 165A of second housing 14. Flap magnet 24 is shown in an opened position, hingedly open at an angle shown and described by the curved line 40.

When flap magnet 24 is opened, the upper left corner 176 of the flap magnet 24 may touch a point 172 of the bottom 152 of annular shoulder 80. Additionally, point 178 on the top 36 of the flap magnet 24 may touch the point 174 on the bottom 153 of flat annular ring 81. Further, the lower 38 right corner 180 of flap magnet 24 may touch at point 182 or nearby by intersecting a point 182 on the pair of perpendicular narrow strips 74 which traverse the bottom opening 72 of the flap magnet retention device 26.

Flap magnet 24 may hingedly open in any radial direction, point 172 may be anywhere in a ring of positions located on the bottom 152 of the annular shoulder 80. FIG. 8B shows one possible configuration with the flap magnet 24 opened. As such, the previous paragraph describes what is shown in FIG. 8B. The flap magnet 24 could be oriented where the upper right corner 184 would be intersecting a point at the bottom 152 of annular shoulder 80. In this case, the flap magnet 24 would be opening 180 degrees (not shown) from the orientation shown in FIG. 8B.

FIG. 9 is a perspective view of the magnet housing 20 showing the four openings 98 in which the urine flow 120 enters, to further pass through the central urine passageway 105 located centrally and through the shoulder 80. The urine flows through the plurality of openings 98, passes down through the central urine passageway 105 and comes in contact with the top 36 of the lower magnet 24. When the urine fluid 120A in the urine flow path 120 reaches a critical force value which overcomes the magnetic attraction between the stationary magnet 22 and flap magnet 24, the flap magnet 24 angularly opens as if on a hinge. Thereafter when the urine fluid 120A is emptied, flap magnet 24 returns to the closed position closing the central urine passageway 105 once the forces of the urine fluid 120A in the urine flow path 120 falls below the critical value. Because of the tornado or vortex effect in chamber 17 the urine flow 120 will continue and allow the urine above flow magnet 24 to empty into chamber 17 and be discharged from the urine control device 10.

FIG. 10A is a side view of magnet housing 20 of the urine control device 10. The top 151 of annular shoulder 80 connects through the four openings 98 in the magnet housing 20 to the central urine passageway aperture 105. The top 151 of the annular shoulder 80 acts as a floor which passes into the interior of the magnet housing 20 to the central urine passageway aperture 105.

Figure 10B:
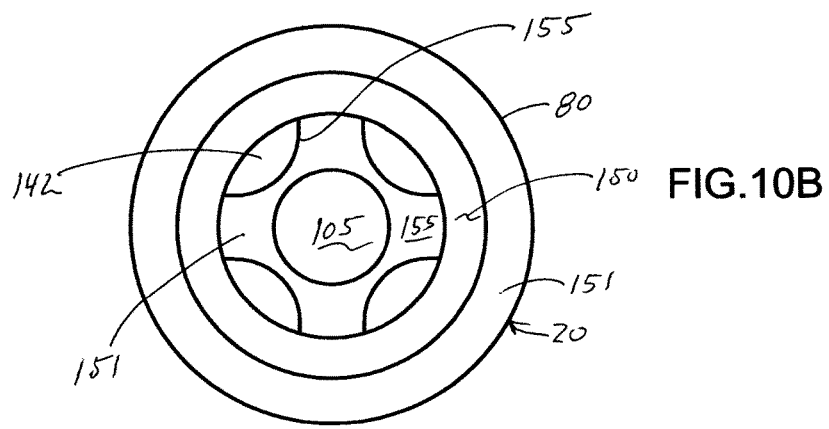
FIG. 10B is a top view of the magnet housing of the urine control device.
Figure 10A:
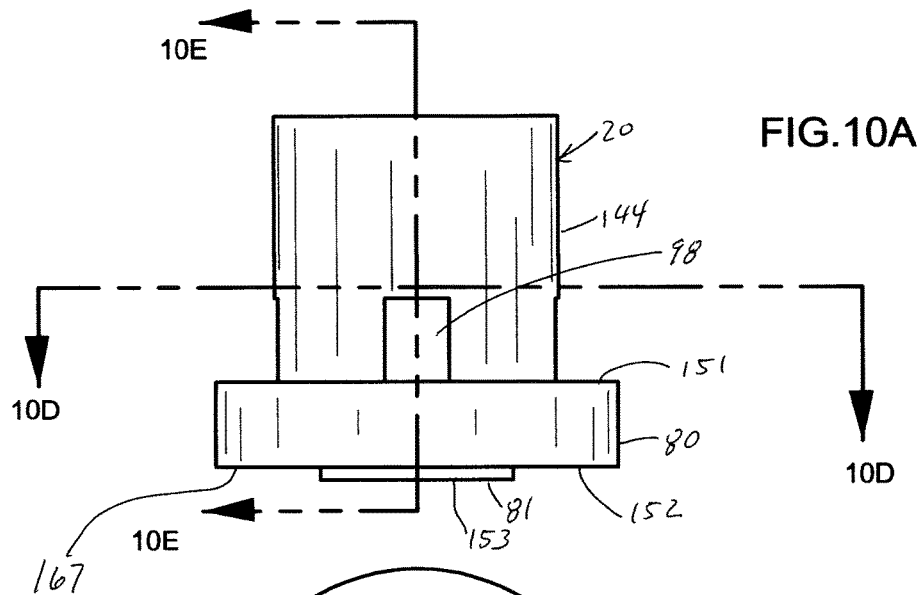
FIG. 10A is a side view of the magnet housing of the urine control device.

FIG. 10B is a top view of the magnet housing of the urine control device 10 with the stationary magnet 22 removed. It can be seen that the top 151 of the annular shoulder 80 passes into the interior of the magnet housing 20 to the central urine passageway aperture 105. Four vertical columns 155 are shown about 90 degrees apart, the bottom 34 of the stationary magnet 22 would rest on the top 142 of each of these four vertical columns 155. An upper lip 150 is shown which would hold the top 32 of the stationary magnet 22 keeping the stationary magnet 22 fixed intermediate the upper lip 150 and the top of the four columns 155. The upper lip 150 also ensures that the urine flow 120 does not enter the portion of the magnet housing 20 where the stationary magnet 22 resides.

Figure 10C:
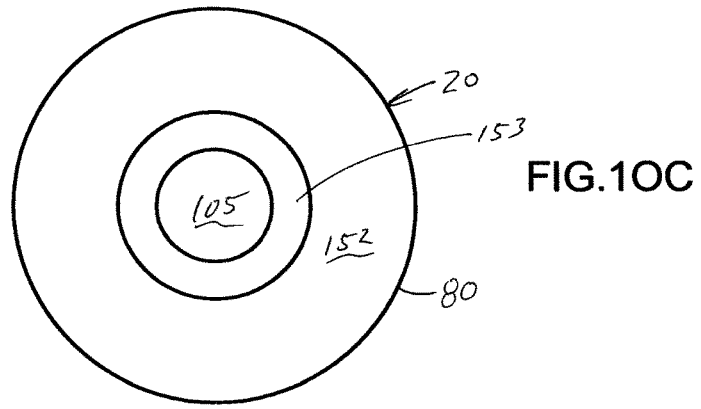
FIG. 10C is a bottom view of the magnet housing of the urine control device.

FIG. 10C is a bottom view of the magnet housing 20 of the urine control device 10. The central urine passageway aperture 105 is shown passing through both the annular shoulder 80 and the flat annular ring 81 which depends centrally from the bottom 152 of the annular shoulder 80. The bottom 153 of the flat annular ring 81 is shown.

Figure 10D:
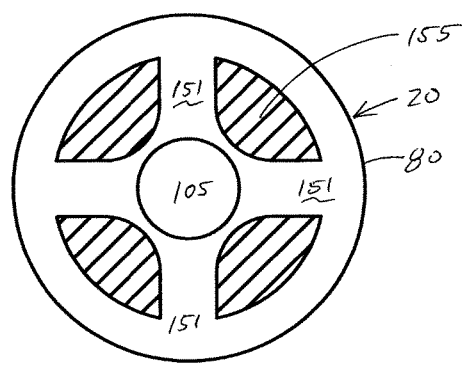
FIG. 10D is a view of the magnet housing of the urine control device taken along lines 10D-10D of FIG. 10A.

FIG. 10D is a view of the magnet housing of the urine control device taken along lines 10D-10D of FIG. 10A. The top 151 of the annular shoulder 80 passes into the interior of the magnet housing 20 to the central urine passageway aperture 105. Four vertical columns 155 are shown in section and about 90 degrees apart, the bottom 34 of the stationary magnet 22 would rest on the top of each of these four vertical support columns 155.

Figure 10E:
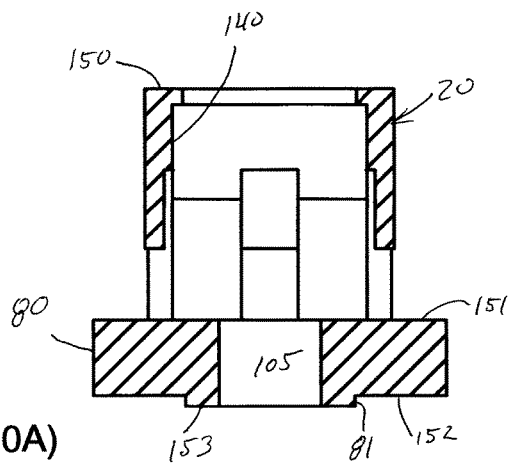
FIG. 10E is a view of the magnet housing of the urine control device taken along lines 10E-10E of FIG. 10A.
Figure 11A:
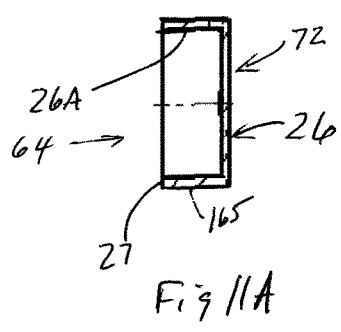
FIG. 11A is a section view taken at line 11A-11A of FIG. 11.
Figure 11:
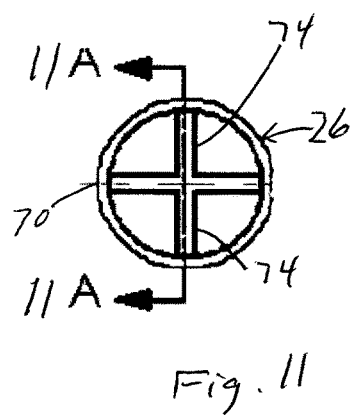
FIG. 11 is a plan view of magnet retention device.

FIG. 10E is a sectional view of the magnet housing 20 of the urine control device 10 taken along lines 10E-10E of FIG. 10A.

The first housing 60 and second housing 14 are connected with twist-lock assemblies to assure the first housing 60 and second housing 14 are connected correctly and without adhesives. The silicone magnet housing 20 acts like a gasket between first housing 20 and lower magnet 24 to prevent leakage when lower magnet 24 is in a closed position.

A urine flow cycle begins with the flap magnet 24 in a closed position. When the fluid pressure reaches 7.5 to 10.5 inches of $H_2O$, the fluid pressure against flap magnet 24 results in a force which overcomes the attraction between the magnet 24 and magnet 22 and opens flap magnet 24. The force that opens flap magnet 24 is from the fluid pressure zone P1 in the chamber 88, which forces flap magnet 24 into an open position. Once the flap magnet is open, the fluid pressure P1 zone is above the restricted passageway of annular opening 105. P1 is within chamber 88 and is shown at FIG. 8A. Fluid pressure P2 in the restricted passageway of annular aperture or opening 105 is greater than fluid pressure P1 within chamber 88 because of the fluid flowing through the restricted annular opening 105. According to the Bernoulli effect, the velocity of the fluid at the restricted area 105 is faster than the fluid speed in chamber 88 and the area above the annular opening 105. Just downstream and below the opening 105, the fluid pressure at P3 is lower or less than fluid pressure P2. This lower pressure P3 causes an increase in the velocity of fluid in the chamber 17. The bowl-shape of chamber 17 causes a vortex fluid effect in chamber 17. This vortex can only be maintained with lower pressure P3 and increased speed of the fluid. The low pressure area p3 pulls the fluid from above the restricted annular opening 105 and evacuates the remaining fluid above the restricted annular opening 105 while keeping the flap magnet 24 open. The increased velocity of the fluid at the restricted annular opening 105 keeps flap magnet 24 open for a longer period of time counter to the magnetic attraction force between the stationary magnet 22 and flap magnet 24. The force resulting from the flowing fluid at opening 105 overcomes the magnetic attraction and keeps magnet 24 open while the remaining fluid drains from the bladder and housing 60. Further, as the fluid leaves chamber 17 it pulls outside air into passageway 86 which decreases the fluid pressure which allows the fluid to drain into the collection bag pulling outside air through opening 28 which results in microscopic air bubbles being pulled into the fluid stream in passageway 86 and into collection bag 110.

When the fluid 120 above the flap magnet is drained into chamber 17 and there is little or no fluid left above flap magnet 24, then flap magnet closes against the magnet housing 20 and the cycle starts over. New fluid enters the bladder 112 and the fluid in the bladder drains to the first housing 60. When the fluid pressure reaches the critical value of 7.5-10.5 inches of $H_2O$ against the flap magnet 24, the flap magnet 24 opens again.

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

I claim:

1. A flow control device comprising:
   a magnet housing having a stationary magnet disposed therein, said magnet housing having an aperture formed therein, said magnet housing having an annular ring surrounding said aperture;
   a flap magnet disposed against said magnet housing and for being attracted to said stationary magnet and held against said annular ring counter to pressure of a fluid in the flow control device, said stationary magnet and said flap magnet sized for having an attraction force set to a predetermined value, which when exceeded by the pressure of the fluid acting on said flap magnet at said annular aperture results in the flap magnet pivoting away from said aperture at an angle while remaining at least partially in contact with said magnet housing.

2. The flow control device according to claim 1, comprising:
   a flap magnet retention device disposed in an outlet housing opening for preventing said flap magnet from dropping and losing contact with said magnet housing.

3. The flow control device according to claim 2, wherein said flap magnet retention device defines a distance to said magnet housing which limits the angle said flap magnet pivots to less than 45 degrees.

4. The flow control device according to claim 2, wherein said magnet retention device has an inside wall, a diameter of said flap magnet is greater than a largest distance between said inside wall and an edge of said aperture, such that said flap magnet cannot be positioned against said magnet housing without completely covering said annular aperture.

5. The flow control device according to claim 2, wherein said outlet housing defines an annular bowl-shaped chamber leading to a drain aperture at a base of said bowl-shaped chamber, said bowl-shaped chamber has an annular wall region extending longitudinally from said drain aperture.

6. The flow control device according to claim 5, wherein said bowl-shaped chamber is free of any structures, within said annular wall region, which would disrupt a vortex flow.

7. The flow control device according to claim 6, wherein said annular wall region extends substantially up to said magnet retention device.

8. The flow control device according to claim 6, wherein said magnet retention device has an inside wall and strips that extend between opposite points on said inside wall, said strips prevent said flap magnet from being separated from said magnet housing.

9. The flow control device according to claim 1, wherein said predetermined value is set to release when a pressure of 7.5-10.5 inches of $H_2O$ is realized against said flap magnet.

* * * * *